(12) United States Patent
Abe

(10) Patent No.: US 11,703,934 B2
(45) Date of Patent: Jul. 18, 2023

(54) EXERCISE INFORMATION ACQUISITION EQUIPMENT

(71) Applicant: CASIO COMPUTER CO., LTD., Tokyo (JP)

(72) Inventor: Yuji Abe, Komae (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 812 days.

(21) Appl. No.: 16/576,981

(22) Filed: Sep. 20, 2019

(65) Prior Publication Data

US 2020/0100730 A1    Apr. 2, 2020

(30) Foreign Application Priority Data

Oct. 1, 2018  (JP) ................................. 2018-186512

(51) Int. Cl.
  *G06F 1/32* (2019.01)
  *A63B 24/00* (2006.01)
  (Continued)

(52) U.S. Cl.
  CPC ............ *G06F 1/325* (2013.01); *A61B 5/0002* (2013.01); *A61B 5/6833* (2013.01);
  (Continued)

(58) Field of Classification Search
  CPC ... A63B 24/0062; G06F 1/3212; G06F 1/325; G06F 1/163
  See application file for complete search history.

(56) References Cited

U.S. PATENT DOCUMENTS

2015/0335947 A1* 11/2015 Kaushansky .......... G16H 40/63
                                                           340/870.07
2016/0332025 A1* 11/2016 Repka ..................... G06F 3/014
                                (Continued)

FOREIGN PATENT DOCUMENTS

JP         2004230152 A      8/2004
JP         2014182063 A      9/2014
                (Continued)

OTHER PUBLICATIONS

Japanese Office Action dated Sep. 15, 2020 (and English translation thereof) issued in Japanese Application No. 2018-186512.

*Primary Examiner* — Jaweed A Abbaszadeh
*Assistant Examiner* — Cheri L Harrington
(74) *Attorney, Agent, or Firm* — Holtz, Holtz & Volek PC

(57) ABSTRACT

An exercise information acquisition equipment of the present invention is an electronic equipment which builds therein a battery, is driven with electric power of the battery and acquires information relating to an exercise that a user performs and includes a battery remaining amount acquisition device which acquires a battery remaining amount of the battery, a time information acquisition device which acquires information relating to a time taken for the exercise which is information that how long the user plans to perform the exercise and an electric power control device which controls an operation pertaining to a power consumption reduction of the electronic equipment on the basis of the battery remaining amount and the information relating to the time taken for the exercise.

20 Claims, 4 Drawing Sheets

(51) Int. Cl.
*G06F 1/16* (2006.01)
*G06F 1/3234* (2019.01)
*A61B 5/00* (2006.01)
*A63H 33/04* (2006.01)
*G06F 1/3212* (2019.01)

(52) U.S. Cl.
CPC ............ *A61B 5/6843* (2013.01); *A61B 5/721* (2013.01); *A63B 24/0062* (2013.01); *A63H 33/042* (2013.01); *G06F 1/163* (2013.01); *G06F 1/3212* (2013.01)

(56) References Cited

U.S. PATENT DOCUMENTS

| | | | | |
|---|---|---|---|---|
| 2017/0086738 | A1* | 3/2017 | Kudo | A61B 5/7282 |
| 2018/0113498 | A1* | 4/2018 | Cronin | A61B 5/1118 |

FOREIGN PATENT DOCUMENTS

| | | | | |
|---|---|---|---|---|
| JP | 2017062126 | A | 3/2017 | |
| JP | 2017063946 | A | 4/2017 | |
| JP | 2017106808 | A | 6/2017 | |
| WO | WO-9963360 | A2 * | 12/1999 | G01C 21/16 |

\* cited by examiner

FIG. 3

| SAMPLING RATE (Hz) | MEASURABLE TIME INFORMATION (Sec) PER 1% OF BATTERY |
|---|---|
| 60 | 60 |
| 55 | 65 |
| 50 | 70 |
| 45 | 75 |
| 40 | 80 |
| 35 | 85 |
| 30 | 90 |

EXERCISE INFORMATION ACQUISITION EQUIPMENT

CROSS REFERENCE TO RELATED APPLICATIONS

This application is based upon and claims the benefit of priority under 35 USC 119 of Japanese Patent Application No. 2018-186512 filed on Oct. 1, 2018 the entire disclosure of which, including the description, claims, drawings, and abstract, is incorporated herein by reference in its entirety.

BACKGROUND

1. Field

The present invention relates to an exercise information acquisition equipment.

2. Related Art

Nowadays, sensing of an exercise amount, a motion and vital information of an athlete is performed by a wearable sensor (for example, see Japanese Patent Application Laid Open No. 2017-106808).

Then, it is disclosed in Japanese Patent Application Laid Open No. 2017-106808 that in a case where a battery remaining amount of the wearable sensor is lowered, extension of a driving time is promoted by stopping driving of a sensor which is large in power consumption and/or decreasing a sampling rate.

SUMMARY

According to one aspect of the present invention, there is provided an exercise information acquisition equipment which includes a battery remaining amount acquisition device which acquires a battery remaining amount of a battery which is built in the exercise information acquisition equipment, a time information acquisition device which acquires information relating to an exercise time which is information that how long a user plans to perform the exercise and an electric power control device which controls an operation pertaining to a reduction in power consumption of the exercise information acquisition equipment on the basis of the battery remaining amount and the information relating to the exercise time, in which in a case where the battery remaining amount is sufficiently appropriate for the time to be taken for the exercise that the user plans to perform, the electric power control device does not perform the operation pertaining to the reduction in power consumption of the exercise information acquisition equipment.

BRIEF DESCRIPTION OF THE DRAWINGS

FIG. 3 is a diagram illustrating one example of a management table which is stored in a storage device of the exercise information acquisition equipment according to one embodiment of the present invention.

DETAILED DESCRIPTION

In the following, an exercise information acquisition equipment (an electronic equipment) 1 according to one embodiment of the present invention will be described with reference to the appended drawings.

Figure 1:
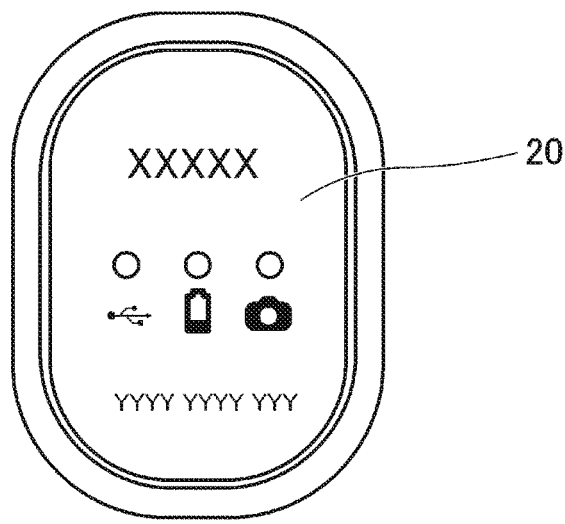
FIG. 1 is a diagram illustrating one example of an exercise information acquisition equipment (an electronic equipment) according to one embodiment of the present invention.
Figure 2:
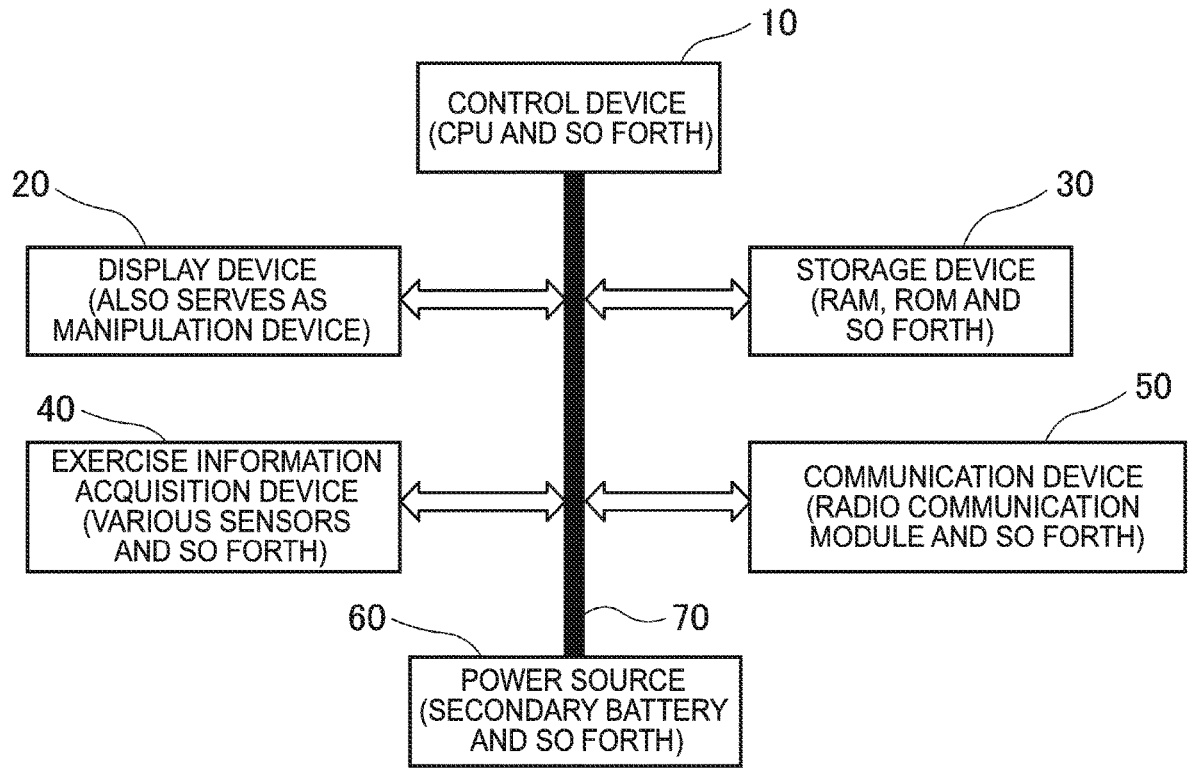
FIG. 2 is a block diagram illustrating one example of the exercise information acquisition equipment according to one embodiment of the present invention.

FIG. 1 is a diagram illustrating one example of the exercise information acquisition equipment 1 according to one embodiment of the present invention, FIG. 2 is a block diagram illustrating one example of the exercise information acquisition equipment 1 according to one embodiment of the present invention and FIG. 3 is a diagram illustrating one example of a management table which is stored in a storage device 30 of the exercise information acquisition equipment 1 according to one embodiment of the present invention.

The exercise information acquisition equipment 1 according to the present embodiment is a wearable type electronic equipment 1 which is attachable to an arm and/or the waist of a user and includes a control device 10, a display device 20 which also functions as a manipulation device, a storage device 30, an exercise information acquisition device 40, a communication device 50 and a power source 60 and the above-described devices are connected together via a data bus 70 to be data-communicable with one another as illustrated in FIG. 2.

The control device 10 includes, for example, a CPU (Central Processing Unit) and so forth and functions as a device which is in charge of general control of the exercise information acquisition equipment 1 and executes various processes which will be described later in accordance with an operation program which is stored in the storage device 30.

The display device 20 is configured by a liquid crystal display device and so forth having a touch panel function and not only performs various kinds of display but also functions as the manipulation device that the user uses for manipulation of the exercise information acquisition equipment 1.

Incidentally, it is not necessary to limit the display device 20 to the liquid crystal display device and the display device 20 may be a display device and so forth having the touch panel function which is achieved by using an organic EL (Electroluminescent) display on a display unit.

The storage device 30 includes a RAM (Random Access Memory), a ROM (Read Only Memory) and so forth and various programs which are used for execution of operations of the exercise information acquisition equipment 1 are stored in the storage device 30.

In addition, as will be described later, the storage device 30 also stores data and so forth which are acquired by the exercise information acquisition device 40 and also stores a management table (see FIG. 3) that predetermined sampling rates of a sensor which measures an exercising state of the user as the exercise information acquisition device 40 are set in one-to-one correspondence with pieces of measurable time information per predetermined capacity of the power source 60 (a secondary battery and so forth) respectively.

For example, as illustrated in FIG. 3, in the present embodiment, the management table is of the type of recording measurable time information which indicates how long measurement of the exercising state of the user is possible in a case where a predetermined capacity of the power source 60 (the secondary battery) is set to 1% and the sampling rate of the sensor which functions as the exercise information acquisition device 40 is changed from 60 Hz to 30 Hz 5 Hz-by-5 Hz with the battery capacity of 1%.

Accordingly, although details will be described later, since the management table is stored in the storage device 30, it becomes possible to perform calculations as to which sampling rate is to be selected in order to perform measurement of the exercising state of the user for a necessary measurement time from the battery remaining amount of the power source 60 (the secondary battery).

The exercise information acquisition device 40 is the sensor and so forth used for measurement of the exercising state of the user (acquisition of information relating to the exercise that the user performs) and a sensor which measures, for example, an acceleration, an orientation, rotation, an inclination, position information (GPS: Global Positioning System), a temperature or a humidity is given as the sensor which functions as the exercise information acquisition device 40.

Incidentally, it goes without saying that a sensor or sensors other than the above-described sensor(s) may be used.

Then, for example, in a case where the exercise information acquisition device 40 is configured by the sensor which measures the position information (GPS), it becomes possible to acquire the position information as information relating to the exercise of the user in a case where the user is performing the exercise such as jogging and so forth and it becomes possible to obtain an average running speed from the position information.

In addition, for example, in a case where the exercise information acquisition device 40 is configured by the temperature sensor, it becomes possible to acquire a temperature of an exercise environment as the information relating to the exercise of the user in a case where the user is performing the exercise such as jogging and so forth.

Incidentally, the exercise information acquisition device 40 may be configured by a plurality of sensors and the exercise information acquisition device 40 may be configured by, for example, two sensors which measure the acceleration and the position information (GPS) respectively.

Incidentally, although a case where the exercise that the user performs mainly is jogging and so forth (a running exercise including walking) is described here, it goes without saying that the exercise that the user performs may be other exercises such as golf, swimming, dancing, soccer, baseball and so forth and there is no particular limitation to the kind of the exercise to be performed.

The communication device 50 is a radio communication module and so forth via which data communication with an external equipment such as, for example, a smartphone and so forth becomes possible and plays a role of transmitting information (data) relating to the exercise of the user which is acquired by the exercise information acquisition device 40 and is stored into the storage device 30 to the smartphone and so forth.

In addition, the communication device 50 also plays a role of receiving data which is sent from the external equipment such as, for example, the smartphone and so forth to the exercise information acquisition equipment 1 as will be described later.

The power source 60 is a secondary battery which is a so-called battery and so forth and is a part which is adapted to supply electric power with which the exercise information acquisition equipment 1 is driven.

Incidentally, in the following, there are cases where the power source 60 is described simply as the battery.

Next, operations and so forth of the exercise information acquisition equipment 1 which are executed so as to make it possible to record information relating to the exercise that the user performs even in a case where the battery remaining amount is not sufficient will be described in detail with reference to flowcharts.

Figure 4:
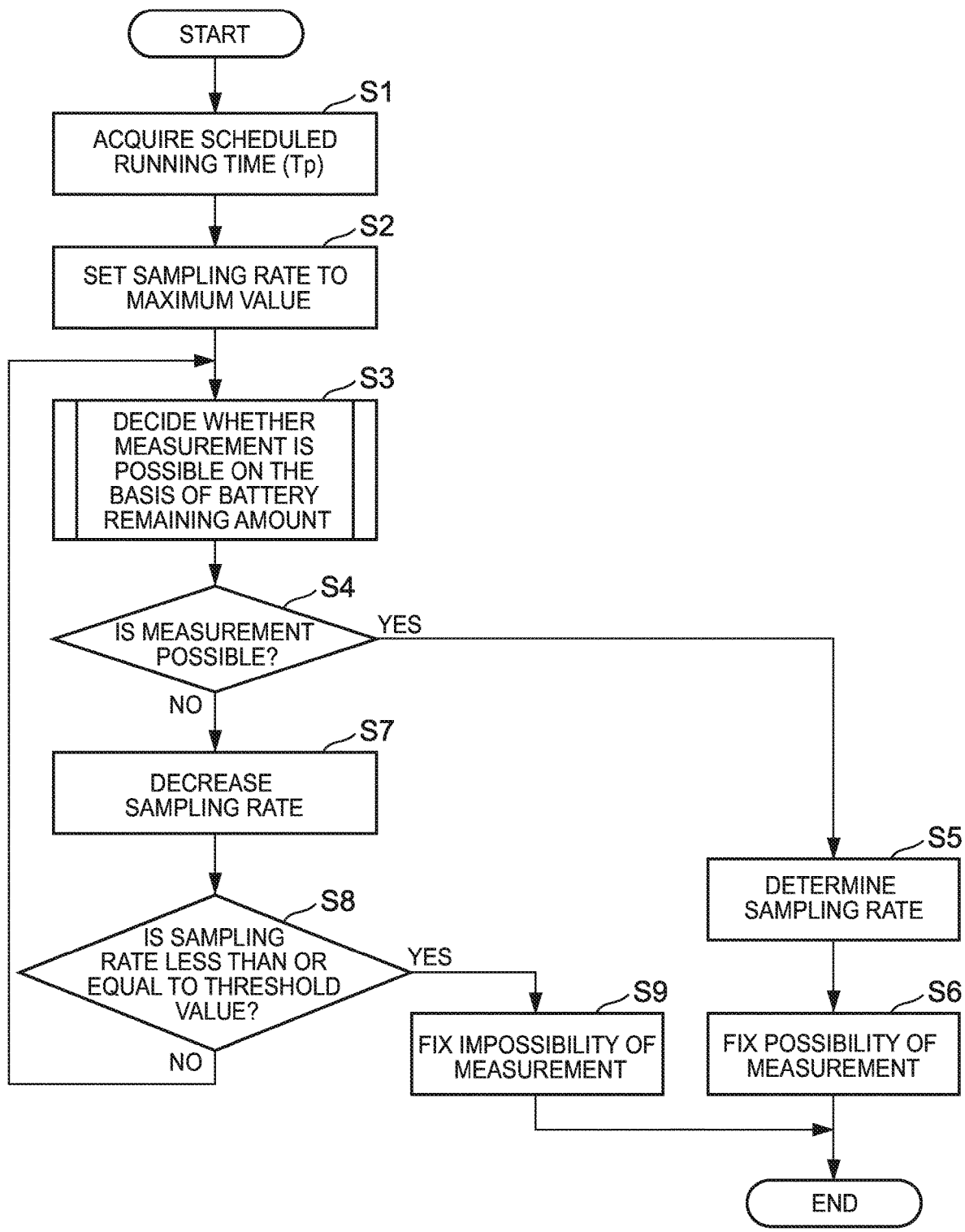
FIG. 4 is a main flowchart for explaining one example of operations of the exercise information acquisition equipment according to one embodiment of the present invention.
Figure 5:
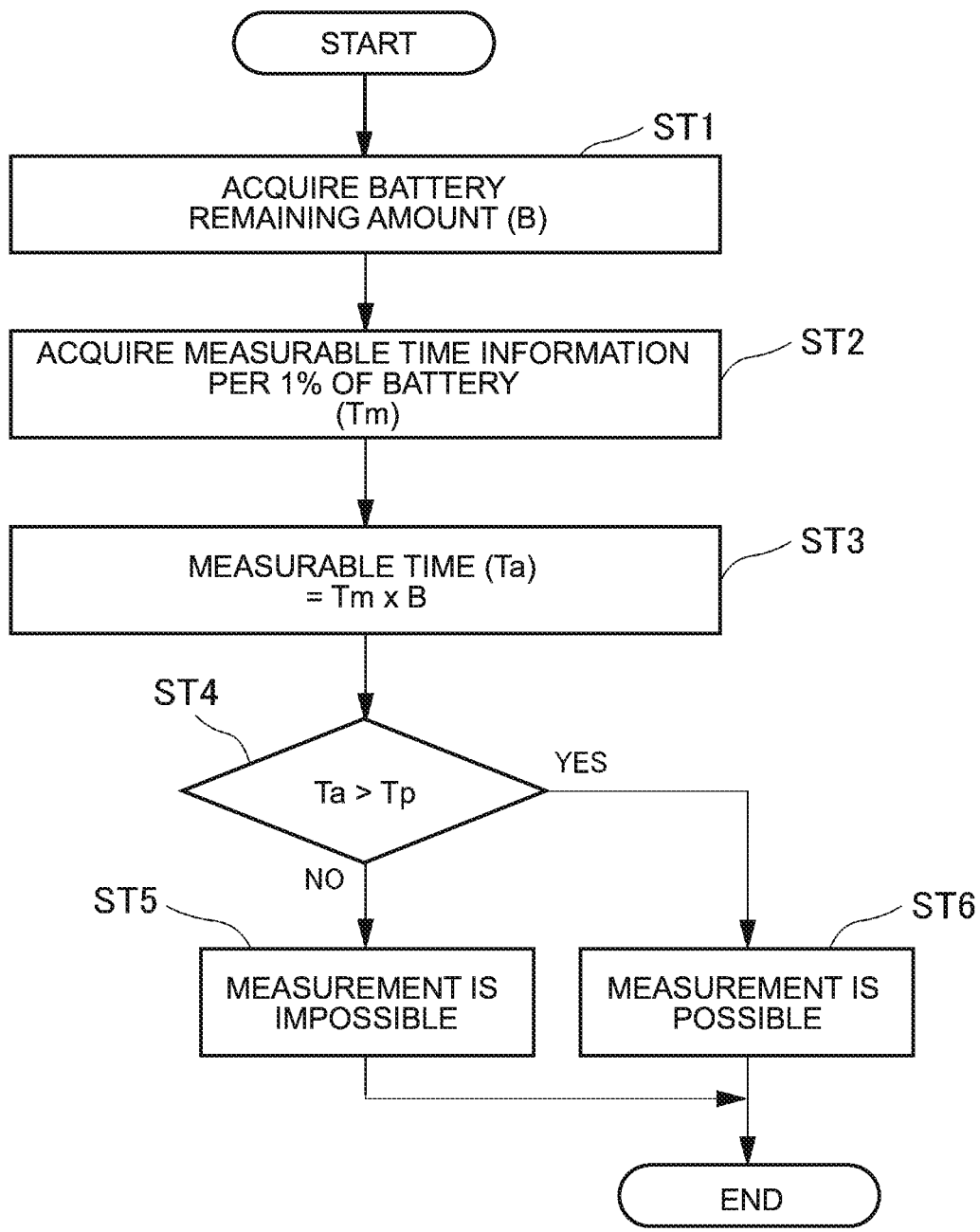
FIG. 5 is a sub flowchart for explaining one example of an operation in step S3 in the main flowchart.

FIG. 4 is a main flowchart for explaining one example of the operations of the exercise information acquisition equipment 1 and FIG. 5 is a sub flowchart for explaining one example of an operation in step S3 in the main flowchart.

Incidentally, although detailed description is omitted, after termination of execution of processes which will be described with reference to FIG. 4 and FIG. 5, the user performs the exercise with the exercise information acquisition equipment 1 being attached to his/her body and thereby the exercise information acquisition equipment 1 acquires the information relating to the exercise by the exercise information acquisition device 40 and the acquired information relating to the exercise is stored into the storage device 30 as data.

In a case where the user manipulates the smartphone and so forth so as to input information relating to an exercise time (the exercise time taken for an exercise that the user plans to perform) and then manipulates the smartphone and so forth so as to transmit the information relating to the exercise time to the exercise information acquisition equipment 1, execution of the flowchart illustrated in FIG. 4 is started.

Here, the information relating to the exercise time is information that how long the user plans to perform the exercise such as, for example, jogging (a running exercise including walking). In a case where the user plans to perform jogging for one hour, information that the exercise time is one hour is transmitted to the exercise information acquisition equipment 1 via the smartphone and so forth as the information relating to the exercise time and execution of the flowchart illustrated in FIG. 4 is started.

Then, the communication device 50 functions as a time information acquisition device which acquires the information relating to the exercise time and acquires the information relating to the exercise time (a scheduled running time for running that the user plans to perform) (step S1).

Incidentally, the display device 20 having the touch panel function may be utilized in such a manner that the user is able to input the information relating to the exercise time into the exercise information acquisition equipment 1. In this case, the display device 20 functions as the time information acquisition device.

Then, next, the control device 10 sets the sampling rate to a maximum value (step S2).

For example, the maximum value of the sampling rate is 60 Hz in the present embodiment. Therefore, the sampling rate in a case where the exercise information acquisition device 40 acquires the information relating to the exercise that the user plans to perform is set to 60 Hz.

Then, the flow proceeds to step S3 and whether measurement of the exercising state of the user is possible in the scheduled running time, that is, the exercise time which is scheduled on the basis of the battery remaining amount is decided in accordance with the flowchart illustrated in FIG. 5.

In the following, description will be made assuming that, for example, the user plans to perform jogging for one hour (3,600 seconds) and the battery remaining amount is 50% for easy understanding.

When proceeding to step S3, first, the control device 10 functions as a battery remaining amount acquisition device which acquires the battery remaining amount of the exercise information acquisition equipment 1 and acquires the battery remaining amount 50% (step ST1) as illustrated in FIG. 5.

Then, the control device 10 acquires the measurable time information per predetermined capacity of the battery at 60 Hz which is the sampling rate which was set in step S2 before (step ST2).

Specifically, the control device 10 refers to the management table illustrated in FIG. 3 and acquires 60 seconds which is the measurable time information (second) per 1% which is the predetermined capacity of the battery in a case where the sampling rate which is set in advance is 60 Hz.

Next, the control device 10 functions as an electric power control device which controls an operation pertaining to a reduction in power consumption of the exercise information acquisition equipment 1 on the basis of the battery remaining amount (50%) and the information relating to the exercise time (3,600 seconds), and first calculates the measurable time at 60 Hz which is the sampling rate which is set in advance on the basis of the measurable time information (60 seconds) per predetermined capacity of the battery which corresponds to the sampling rate (60 Hz) which is set in advance and the battery remaining amount (50%) (step ST3).

For example, in the example in FIG. 5, the measurable time is calculated as 3,000 seconds (=60 (second)×50(%)).

Then, the control device 10 which functions as the electric power control device compares the measurable time with the scheduled running time (step ST4) and in a case where the measurable time is shorter than the scheduled running time (step St4: NO), decides that measurement is impossible (step ST5), and in a case where the measurable time is longer than the scheduled running time (step ST4: YES)), decides that the measurement is possible (step ST6).

In the example in FIG. 5, since the measurable time is 3,000 seconds and on the other hand the scheduled running time is 3,600 seconds, it is decided that the measurement is impossible and the flow returns to the flowchart illustrated in FIG. 4.

When returning to the flowchart illustrated in FIG. 4, the control device 10 which functions as the electric power control device decides whether the measurement is possible (step S4) and then in a case where it is decided that the measurement is possible (step S4: YES), determines the sampling rate to the currently set sampling rate (60 Hz) (step S5) and fixes that the measurement is possible at the determined sampling rate (60 Hz) (step S6) and terminates execution of the process.

Incidentally, in terminating execution of the process, the control device 10 makes the communication device 50 notify the external equipment that the user manipulated before so as to input the scheduled running time such as the smartphone and so forth that the measurement is possible at the determined sampling rate in the present embodiment.

On the other hand, in the example in FIG. 5, since the measurable time 3,000 seconds and on the other hand the scheduled running time is 3,600 seconds as described above, it is decided that the measurement is impossible and the flow returns to the flowchart illustrated in FIG. 4. Accordingly, the control device 10 which functions as the electric power control device decides that the measurement is not possible (step S4: NO) in decision of whether the measurement is possible (step S4) and therefore the flow proceeds to step S7.

Then, the control device 10 which functions as the electric power control device executes setting for decreasing (lowering) the sampling rate.

Specifically, a predetermined sampling rate is set to 5 Hz and the control device 10 which functions as the electric power control device sets the sampling rate to 55 Hz which is lowered from the sampling rate (60 Hz) which is set in advance by the predetermined sampling rate (5 Hz).

Then, the control device 10 which functions as the electric power control device decides whether the newly set sampling rate (55 Hz) is less than or equal to a sampling rate threshold value which is set in advance (step S8) and in a case where the newly set sampling rate is less than or equal to the threshold value (step S8: YES), fixes that the measurement is impossible (step S9) and terminates execution of the process in FIG. 4.

Incidentally, in the example in FIG. 4, in terminating execution of the process, the control device 10 makes the communication device 50 notify the external equipment that the user manipulated before so as to input the scheduled running time such as the smartphone and so forth that the measurement is impossible with the current battery remaining amount in the present embodiment.

However, in a case where the communication device 50 is utilized as a notification device which notifies the user of information and the sampling rate that the control device 10 which functions as the electric power control device lowers is below the predetermined sampling rate, the display device 20 may be utilized as the notification device and/or a voice output device (not illustrated) such as a loudspeaker and so forth that the exercise information acquisition equipment 1 includes may be utilized as the notification device, not limited to notifying the user that the measurement is impossible by the communication device 50 which functions as the notification device.

On the other hand, in a case where the newly set sampling rate is not less than or equal to the threshold value (step S8: NO), the flow returns to step S3 and the processes which are the same as the above-described processes are executed.

In the example in FIG. 4, the measurable time reaches 3,250 seconds at the sampling rate of 55 Hz, the measurable time reaches 3,500 seconds at the sampling rate of 50 Hz and the measurable time reaches 3,750 seconds at the sampling rate of 45 Hz. Therefore, as a result of executing the process of returning from step S8 to step S3 a plurality of times, the measurable time becomes longer than the scheduled running time when setting the sampling rate to 45 Hz and thereby execution of the process is terminated via step S5 and step S6.

In the exercise information acquisition equipment 1 according to the present embodiment, even in a case where it seems that there is no sufficient battery remaining amount when seeing display of the battery remaining amount, the control device 10 which functions as the electric power control device controls the sampling rate of the sensor which measures the exercising state of the user as the exercise information acquisition device 40 in such a manner that the measurement is made possible only for the scheduled time of the exercise concerned before the user begins to perform the exercise in this way. Therefore, it becomes possible to suppress run out of battery while the user is performing the exercise.

Although the exercise information acquisition equipment 1 of the present invention is described on the basis of one specific embodiment as above, the present invention is not limited to the above-mentioned specific embodiment.

For example, the average running speed of running exercises that the user performed in the past may be stored into the storage device 30 of the exercise information acquisition equipment 1 and the scheduled running time may be obtained from the average running speed and a scheduled running distance of running that the user plans to perform.

Incidentally, the average running speed of the running exercises that the user performed in the past may be stored not into the storage device 30 but into the external equipment such as the smartphone and so forth.

For this purpose, the present invention may be also embodied in such a manner the control device 10 functions as an average running speed acquisition device so as to acquire the average running speed of the running exercises that the user performed in the past from the storage device 30 and the communication device 50 which functions as the time information acquisition device acquires the scheduled running distance of running that the user plans to perform and to acquire (obtain) the scheduled running time on the basis of the average running speed and the scheduled running distance.

In addition, in the above-described embodiment, the operation pertaining to the power consumption reduction is controlled by controlling the sampling rate of the sensor which measures the exercising state of the user as the exercise information acquisition device 40. However, it is not necessary to limit to the control of the sampling rate and the operation pertaining to the power consumption reduction may be controlled by, for example, stopping a function which has no influence on acquisition of the information relating to the exercise that the user performs and/or turning off display on the display device 20.

The present invention is not limited to the above-mentioned embodiment as above and various modifications and alterations are included within a range that an object of the present invention is achieved and it is obvious to a person skilled in the art that the various modifications and alterations are included from the description of the appended claims.

What is claimed is:

1. An electronic device comprising:
   a sensor which acquires information related to a user's activity at a sampling rate that is set to a predetermined value; and
   a processor which is configured to:
   acquire a first information indicating a battery remaining amount of a battery which supplies power to the electronic device;
   acquire a second information indicating a scheduled activity time which is information indicating how long the user plans to perform an activity;
   set the predetermined value of the sampling rate of the sensor based on the first information and the second information;
   acquire, from a memory, a first measurable time per predetermined fractional unit of a total maximum capacity of the battery and which corresponds to the predetermined value to which the sampling rate of the sensor is set, wherein the memory stores in one-to-one correspondence (i) a plurality of predetermined values for the sampling rate and (ii) a plurality of first measurable times per predetermined fractional unit of the total maximum capacity of the battery, each first measurable time per predetermined fractional unit indicating how long the information related to the user's activity can be acquired by the sensor with the sampling rate being set to the corresponding predetermined value and with the battery remaining amount of the battery being equal to the predetermined fractional unit of the total maximum capacity of the battery, the predetermined fractional unit of the total maximum capacity of the battery being less than the total maximum capacity of the battery, wherein the processor acquires the first measurable time from among the plurality of first measurable times stored in the memory; and
   calculate a second measurable time based on the acquired first information indicating the battery remaining amount of the battery and the acquired first measurable time that corresponds to the predetermined value to which the sampling rate is set.

2. The electronic device according to claim 1, wherein the processor is configured to:
   repeatedly calculate the second measurable time based on the plurality of predetermined values for the sampling rate and the battery remaining amount of the battery; and
   set, as the predetermined value of the sampling rate of the sensor, a largest value among the plurality of predetermined values for which the calculated second measurable time is longer than the scheduled activity time.

3. The electronic device according to claim 1, wherein the processor is configured to:
   control a display to display an image which indicates that measurement is unavailable in response to a determination that the calculated second measurable time is below a predetermined threshold.

4. The electronic device according to claim 1, wherein the processor is configured to:
   control a microphone to output a sound which indicates that measurement is unavailable in response to a determination that the second measurable time is below a predetermined threshold.

5. The electronic device according to claim 1,
   wherein the user's activity is a movement comprising one of walking and running; and
   wherein the scheduled activity time is a time between a start timing of the moving and an end timing of the movement.

6. The electronic device according to claim 1, wherein the predetermined fractional unit is a predetermined percentage of the total maximum capacity of the battery.

7. The electronic device according to claim 1, wherein the predetermined fractional unit is 1% of the total maximum capacity of the battery, whereby each first measurable time per predetermined fractional unit indicates how long the information related to the user's activity can be acquired by the sensor with the sampling rate being set to the corresponding predetermined value and with the battery remaining amount of the battery being equal to 1% of the total maximum capacity of the battery.

8. The electronic device according to claim 5, wherein the processor is configured to:
   store a movement history information to the memory, wherein the movement history information indicates past movement of the user;
   calculate an average speed of the user based on the movement history information which is stored in the memory; and
   acquire the scheduled activity time based on the calculated average speed of the user and a scheduled movement distance inputted by the user.

9. A method of controlling an electronic device that includes a sensor that acquires information related to a user's activity at a sampling rate that is set to a predetermined value, the method comprising:

acquiring, by a processor, a first information indicating a battery remaining amount of a battery which supplies power to the electronic device;

acquiring, by the processor, a second information indicating a scheduled activity time which is information indicating how long the user plans to perform an activity;

setting, by the processor, the predetermined value of the sampling rate of the sensor based on the first information and the second information;

acquiring, by the processor, from a memory, a first measurable time per predetermined fractional unit of a total maximum capacity of the battery and which corresponds to the predetermined value to which the sampling rate of the sensor is set, wherein the memory stores in one-to-one correspondence (i) a plurality of predetermined values for the sampling rate and (ii) a plurality of first measurable times per predetermined fractional unit of the total maximum capacity of the battery, each first measurable time per predetermined fractional unit indicating how long the information related to the user's activity can be acquired by the sensor with the sampling rate being set to the corresponding predetermined value and with the battery remaining amount of the battery being equal to the predetermined fractional unit of the total maximum capacity of the battery, the predetermined fractional unit of the total maximum capacity of the battery being less than the total maximum capacity of the battery, wherein the first measurable time is acquired from among the plurality of first measurable times stored in the memory; and calculating, by the processor, a second measurable time based on the acquired first information indicating the battery remaining amount of the battery and the acquired first measurable time that corresponds to the predetermined value to which the sampling rate is set.

10. The method according to claim 9, wherein the method further comprises:

repeatedly calculating, by the processor, the second measurable time based on the plurality of predetermined values for the sampling rate and the battery remaining amount of the battery; and setting, by the processor, as the predetermined value of the sampling rate of the sensor, a largest value among the plurality of predetermined values for which the calculated second measurable time is longer than the scheduled activity time.

11. The method according to claim 9, wherein the method further comprises:

controlling, by the processor, a display to display an image which indicates that measurement is unavailable in response to a determination that the calculated second measurable time is below a predetermined threshold.

12. The method according to claim 9, wherein the method further comprises:

controlling, by the processor, a microphone to output a sound which indicates that measurement is unavailable in response to a determination that the second measurable time is below a predetermined threshold.

13. The method according to claim 9, wherein the user's activity is a movement comprising one of walking and running; and wherein the scheduled activity time is a time between a start timing of the moving and an end timing of the movement.

14. The method according to claim 13, wherein the method further comprises:

storing, by the processor, a movement history information to the memory, wherein the movement history information indicates past movement of the user;

calculating, by the processor, an average speed of the user based on the movement history information which is stored in the memory; and acquiring, by the processor, the scheduled activity time based on the calculated average speed of the user and a scheduled movement distance inputted by the user.

15. A non-transitory computer readable storage medium storing one or more programs, the one or more programs comprising instructions that are executable by one or more processors of an electronic device that includes a sensor that acquires information related to a user's activity at a sampling rate that is set to a predetermined value, the instructions being executable by the one or more processors to cause the electronic device to:

acquire a first information indicating a battery remaining amount of a battery which supplies power to the electronic device;

acquire a second information indicating a scheduled activity time which is information indicating how long the user plans to perform an activity;

set the predetermined value of the sampling rate of the sensor based on the first information and the second information;

acquire, from a memory, a first measurable time per predetermined fractional unit of a total maximum capacity of the battery and which corresponds to the predetermined value to which the sampling rate of the sensor is set, wherein the memory stores in one-to-one correspondence (i) a plurality of predetermined values for the sampling rate and (ii) a plurality of first measurable times per predetermined fractional unit of the total maximum capacity of the battery, each first measurable time per predetermined fractional unit indicating how long the information related to the user's activity can be acquired by the sensor with the sampling rate being set to the corresponding predetermined value and with the battery remaining amount of the battery being equal to the predetermined fractional unit of the total maximum capacity of the battery, the predetermined fractional unit of the total maximum capacity of the battery being less than the total maximum capacity of the battery, wherein the first measurable time is acquired from among the plurality of first measurable times stored in the memory; and calculate a second measurable time based on the acquired first information indicating the battery remaining amount of the battery and the acquired first measurable time that corresponds to the predetermined value to which the sampling rate is set.

16. The non-transitory computer readable storage medium according to claim 15, wherein the instructions further cause the electronic device to:

repeatedly calculate the second measurable time based on the plurality of predetermined values for the sampling rate and the battery remaining amount of the battery; and set, as the predetermined value of the sampling rate of the sensor, a largest value among the plurality of predetermined values for which the calculated second measurable time is longer than the scheduled activity time.

17. The non-transitory computer readable storage medium according to claim 15, wherein the instructions further cause the electronic device to:

control a display to display an image which indicates that measurement is unavailable in response to a determination that the calculated second measurable time is below a predetermined threshold.

18. The non-transitory computer readable storage medium according to claim 15, wherein the instructions further cause the electronic device to:

control a microphone to output a sound which indicates that measurement is unavailable in response to a determination that the second measurable time is below a predetermined threshold.

19. The non-transitory computer readable storage medium according to claim 15, wherein the user's activity is a movement comprising one of walking and running; and wherein the scheduled activity time is a time between a start timing of the moving and an end timing of the movement.

20. The non-transitory computer readable storage medium according to claim 19, wherein the instructions further cause the electronic device to:

a movement history information to the memory, wherein the movement history information indicates past movement of the user;

calculate an average speed of the user based on the movement history information which is stored in the memory; and acquire the scheduled activity time based on the calculated average speed of the user and a scheduled movement distance inputted by the user.

* * * * *